United States Patent
Edic et al.

(10) Patent No.: US 7,813,473 B2
(45) Date of Patent: Oct. 12, 2010

(54) METHOD AND APPARATUS FOR GENERATING TEMPORALLY INTERPOLATED PROJECTIONS

(75) Inventors: Peter Michael Edic, Albany, NY (US); Bruno De Man, Clifton Park, NY (US); Samit Basu, Niskayuna, NY (US)

(73) Assignee: General Electric Company, Niskayuna, NY (US)

(*) Notice: Subject to any disclaimer, the term of this patent is extended or adjusted under 35 U.S.C. 154(b) by 469 days.

(21) Appl. No.: 10/625,321

(22) Filed: Jul. 23, 2003

(65) Prior Publication Data

US 2004/0120449 A1 Jun. 24, 2004

Related U.S. Application Data

(60) Provisional application No. 60/397,658, filed on Jul. 23, 2002, provisional application No. 60/398,463, filed on Jul. 25, 2002.

(51) Int. Cl.
*A61B 6/03* (2006.01)
*H05G 1/62* (2006.01)

(52) U.S. Cl. .............. 378/8; 378/9; 378/95; 378/197; 600/428

(58) Field of Classification Search .............. 378/4, 378/8, 9, 10, 12, 16, 19, 92, 95, 197; 600/428, 600/425

See application file for complete search history.

(56) References Cited

U.S. PATENT DOCUMENTS

| | | |
|---|---|---|
| 2,340,500 A | 11/1942 | Zunick et al. |
| 4,057,725 A | 11/1977 | Wagner |
| 4,196,352 A | 4/1980 | Berninger et al. |
| 4,274,005 A * | 6/1981 | Yamamura et al. ............ 378/9 |
| 4,384,359 A | 5/1983 | Franke |
| 4,547,892 A | 10/1985 | Richey et al. |
| 4,947,412 A | 8/1990 | Mattson |
| 4,965,726 A | 10/1990 | Heuscher et al. |
| 4,991,190 A | 2/1991 | Mori |
| 5,166,961 A | 11/1992 | Brunnett |
| 5,175,754 A * | 12/1992 | Casey et al. .................... 378/4 |
| 5,228,070 A | 7/1993 | Mattson |
| 5,259,012 A | 11/1993 | Baker et al. |
| 5,262,946 A | 11/1993 | Heuscher |
| 5,276,614 A | 1/1994 | Heuscher |
| 5,305,363 A | 4/1994 | Burke et al. |
| 5,377,249 A | 12/1994 | Wiesent et al. |
| 5,383,231 A * | 1/1995 | Yamagishi .................... 378/15 |
| 5,396,418 A | 3/1995 | Heuscher ............... 364/413.18 |

(Continued)

OTHER PUBLICATIONS

Lalush, David C., Feasibility of Transmission Micro-CT with Two Fan-Beam Sources, IEEE, pp. 1283-1286, Sep. 1-5, 2004, vol. 4, San Francisco, California.

*Primary Examiner*—Allen C. Ho
(74) *Attorney, Agent, or Firm*—Scott J. Asmus

(57) ABSTRACT

A technique is provided for the temporal interpolation of a projection data set acquired of a dynamic object, such as a heart. The projection data set is acquired using a slowly rotating gantry and a distributed X-ray source. The projection data may be interpolated at each view position to a selected instant of time, such as relative to a cardiac phase. The resulting interpolated projection data characterize the projection data at each view location at any instant in time. The set of interpolated projection data may then be reconstructed to generate images and/or volume with improved temporal resolution.

16 Claims, 5 Drawing Sheets

U.S. PATENT DOCUMENTS

| | | | |
|---|---|---|---|
| 5,412,562 A | 5/1995 | Nambu et al. | |
| 5,438,605 A | 8/1995 | Burke et al. | |
| 5,485,493 A | 1/1996 | Heuscher et al. | |
| 5,544,212 A | 8/1996 | Heuscher | |
| 5,570,403 A | 10/1996 | Yamazaki et al. | |
| 5,633,906 A * | 5/1997 | Hell et al. | 378/10 |
| 5,654,995 A | 8/1997 | Flohr | |
| 5,764,721 A | 6/1998 | Light et al. | |
| 5,848,117 A | 12/1998 | Urchuk et al. | |
| 5,966,422 A | 10/1999 | Dafni et al. | |
| 6,047,040 A | 4/2000 | Hu et al. | |
| 6,125,167 A | 9/2000 | Morgan | |
| 6,154,516 A * | 11/2000 | Heuscher et al. | 378/15 |
| 6,183,139 B1 | 2/2001 | Solomon et al. | |
| 6,229,870 B1 * | 5/2001 | Morgan | 378/9 |
| 6,233,308 B1 * | 5/2001 | Hsieh | 378/62 |
| 6,236,705 B1 | 5/2001 | Stergiopoulos et al. | |
| 6,236,709 B1 | 5/2001 | Perry et al. | |
| 6,272,200 B1 * | 8/2001 | Pan et al. | 378/15 |
| 6,333,968 B1 | 12/2001 | Whitlock et al. | |
| 6,353,653 B1 | 3/2002 | Edic | 378/8 |
| 6,381,487 B1 * | 4/2002 | Flohr et al. | 600/425 |
| 6,385,282 B1 | 5/2002 | Francke et al. | |
| 6,421,412 B1 | 7/2002 | Hsieh et al. | |
| 6,453,003 B1 | 9/2002 | Springer et al. | |
| 6,459,755 B1 * | 10/2002 | Li | 378/4 |
| 6,466,640 B1 * | 10/2002 | Taguchi | 378/15 |
| 6,507,639 B1 | 1/2003 | Popescu | |
| 6,510,337 B1 * | 1/2003 | Heuscher et al. | 600/428 |
| 6,522,712 B1 | 2/2003 | Yavuz et al. | 378/4 |
| 6,526,117 B1 * | 2/2003 | Okerlund et al. | 378/8 |
| 6,529,574 B1 * | 3/2003 | Hsieh | 378/4 |
| 6,535,570 B2 | 3/2003 | Dhanantwari et al. | 378/8 |
| 6,674,837 B1 | 1/2004 | Taskar et al. | |
| 6,731,716 B2 | 5/2004 | Mihara et al. | |
| 6,754,300 B2 * | 6/2004 | Hsieh et al. | 378/16 |
| 6,760,399 B2 | 7/2004 | Malamud | |
| 6,807,248 B2 * | 10/2004 | Mihara et al. | 378/10 |
| 6,914,959 B2 | 7/2005 | Bailey et al. | |
| 7,058,440 B2 * | 6/2006 | Heuscher et al. | 600/428 |
| 7,085,342 B2 * | 8/2006 | Younis et al. | 378/8 |
| 7,142,703 B2 * | 11/2006 | Kaufman et al. | 382/131 |
| 7,187,745 B2 * | 3/2007 | Flohr et al. | 378/8 |
| 2002/0074929 A1 | 6/2002 | Taskar et al. | |
| 2002/0085674 A1 | 7/2002 | Price et al. | |
| 2002/0094064 A1 | 7/2002 | Zhou et al. | |
| 2003/0043957 A1 | 3/2003 | Pelc | |
| 2003/0118155 A1 | 6/2003 | Ueno et al. | |
| 2004/0114710 A1 | 6/2004 | Ozaki | |
| 2004/0136490 A1 * | 7/2004 | Edic et al. | 378/4 |
| 2004/0213378 A1 | 10/2004 | Zhou et al. | |
| 2005/0135550 A1 | 6/2005 | De Man et al. | |
| 2005/0175143 A1 | 8/2005 | Miyazaki et al. | |
| 2006/0002506 A1 | 1/2006 | Pelc | |

\* cited by examiner

METHOD AND APPARATUS FOR GENERATING TEMPORALLY INTERPOLATED PROJECTIONS

CROSS-REFERENCE TO RELATED APPLICATIONS

This application claims the benefit of U.S. Provisional Application No. 60/397,658 filed on Jul. 23, 2002 and U.S. Provisional Application 60/398,463 filed on Jul. 25, 2002.

BACKGROUND OF THE INVENTION

The present invention relates generally to the field of medical imaging and more specifically to the field of imaging dynamic, internal tissue, such as cardiac tissue, by computed tomography. In particular, the present invention relates to the generation and reconstruction of temporally interpolated projection data.

Computed tomography (CT) imaging systems measure the attenuation of X-ray beams passed through a patient from numerous angles. Based upon these measurements, a computer is able to reconstruct images of the portions of a patient's body responsible for the radiation attenuation. As will be appreciated by those skilled in the art, these images are based upon separate examination of a series of angularly displaced images of the transmitted X-ray beam. A CT system processes X-ray intensity data to generate 2D maps of the line integral of linear attenuation coefficients of the scanned object at multiple view angle positions, denoted as projection data. These data are then reconstructed to produce an image, which is typically displayed on a monitor, and may be printed or reproduced on film. A virtual 3-D image may also be produced by a CT examination.

CT scanners operate by projecting fan shaped or cone shaped X-ray beams from an X-ray source. The X-ray beams may be collimated to control the shape and spread of the beams. The X-ray beams are attenuated as they pass through the object to be imaged, such as a patient. The attenuated beams are detected by a set of detector elements. Each detector element produces a signal affected by the attenuation of the X-ray beams, and the data are processed to produce signals that represent the line integrals of the attenuation coefficients of the object along the X-ray paths. These signals are typically called "projection data" or just "projections". By using reconstruction techniques, such as filtered backprojection, useful images may be formulated from the projections. The images may in turn be associated to form a volume rendering of a region of interest. The locations of regions of interest, such as pathologies, may then be identified either automatically, such as by a computer-assisted detection (CAD) algorithm or, more conventionally, such as by a trained radiologist. CT scanning provides certain advantages over other types of techniques in diagnosing disease, particularly because it illustrates the accurate anatomical information about the body. Further, CT scans may help physicians distinguish between types of abnormalities more accurately.

CT imaging techniques, however, may present certain challenges when imaging dynamic internal tissues, such as the heart. For example, in cardiac imaging, the motion of the heart causes inconsistencies in the projection data, which, after reconstruction, may result in various motion-related image artifacts such as blurring, streaking, or discontinuities. To reduce the occurrence of motion-related image artifacts, various techniques may be employed to improve the temporal resolution of the imaging system, thereby reducing the effects of the moving tissue. Temporal resolution may generally be improved by decreasing the rotation time of the CT gantry. In this way, the amount of motion that occurs within the temporal window associated with the acquisition of a projection data set is minimized.

Temporal resolution may be further improved by the choice of reconstruction algorithm. For example, segment reconstruction algorithms, such as half-scan reconstruction algorithms, may be employed in the reconstruction process. The segment reconstruction algorithms typically reconstruct images using projection data collected over an angular range of 180° plus the fan angle ($\alpha$) of the X-ray beam. Because the acquisition of projection data during gantry rotation of 180°+$\alpha$ requires less time when compared to acquisition during 360° of gantry rotation, the temporal resolution in the reconstructed images is improved.

Multi-sector reconstruction techniques may also improve the temporal resolution of the reconstructed images by using projection data acquired during multiple rotations of the gantry by a multi-slice detector array. The projection data set used for reconstruction is composed of two or more sectors of projection data that are acquired from different cardiac cycles. The sectors comprise the data acquired during a short span of the gantry rotation, typically less than half of a rotation. The sectors, therefore, have good temporal resolution if acquired by a rapidly rotating gantry, thereby providing a good effective temporal resolution for the aggregate projection data set used in reconstruction.

Using the techniques discussed above, third and fourth generation CT systems are capable of temporal resolutions of approximately 300 ms using segment reconstruction techniques. Fifth generation CT systems, utilizing a stationary detector ring and an electron gun which sweeps an electron beam across a stationary target ring to generate x-rays, are capable of achieving a temporal resolution of approximately 50 ms. A temporal resolution of approximately 20 ms, however, is desirable in order to "freeze" cardiac motion, thereby minimizing motion related artifacts in the reconstructed images. For third generation CT systems, improving temporal resolution by the above techniques has typically focused on further increasing the rotational speed of the gantry.

However, as the rotational speed of the gantry increases, the centripetal force on the gantry components also increases. The increasing centripetal force and the tolerances of the gantry components may comprise, therefore, a mechanical limitation to increases in gantry angular velocity. Furthermore, to obtain consistent image quality in terms of signal-to-noise ratio, a constant X-ray flux should be delivered to the imaged object or patient during the scan interval. Achieving a constant X-ray flux, however, places increased demand on the X-ray tube, particularly in regard to tube output, and on the components that cool the X-ray tube. Both mechanical and X-ray flux considerations, therefore, are obstacles to increasing the gantry rotation speed sufficiently to achieve a temporal resolution of 20 ms or better in CT reconstructions. A technique for achieving a temporal resolution without increasing gantry rotation speed is therefore desirable.

BRIEF DESCRIPTION OF THE INVENTION

The present technique provides a novel method and apparatus for improving temporal resolution of a CT imaging system. The technique employs a slowly rotating distributed X-ray source used to acquire projection data at each view position of an object or patient. The projection data, based upon the cardiac phase data and the frequency content of the projection data, may be filtered and temporally interpolated to generate interpolated projection data corresponding to a particular instant in the cardiac cycle. A high temporal resolution CT image may be reconstructed from the interpolated projection data.

BRIEF DESCRIPTION OF THE DRAWINGS

The foregoing and other advantages and features of the invention will become apparent upon reading the following detailed description and upon reference to the drawings in which.

DETAILED DESCRIPTION OF SPECIFIC EMBODIMENTS

Figure 1:
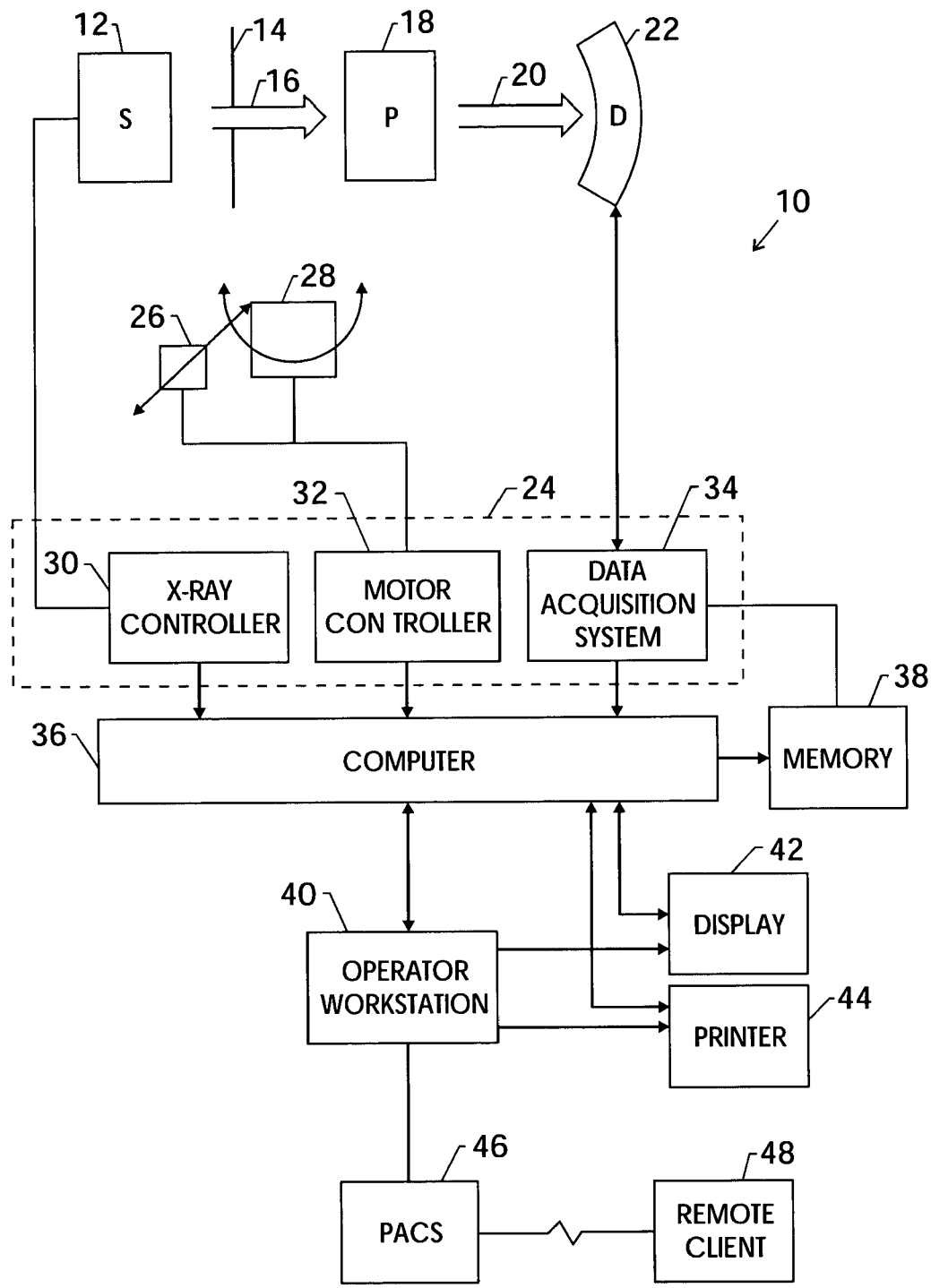
FIG. 1 is a diagrammatical view of an exemplary imaging system in the form of a CT imaging system for use in producing processed images, in accordance with one aspect of the present technique.

FIG. 1 illustrates diagrammatically an imaging system 10 for acquiring and processing image data. In the illustrated embodiment, system 10 is a computed tomography (CT) system designed to acquire X-ray projection data, to reconstruct the projection data into an image, and to process the image data for display and analysis in accordance with the present technique. In the embodiment illustrated in FIG. 1, imaging system 10 includes a distributed source of X-ray radiation 12 positioned adjacent to a collimator 14. In this exemplary embodiment, the distributed source of X-ray radiation 12 comprises one or more addressable X-ray focal spots.

Collimator 14 permits a stream of radiation 16 to pass into a region in which a subject, such as a human patient 18 is positioned. The stream of radiation 16 may be generally cone shaped, depending on the configuration of the detector array, discussed below, as well as the desired method of data acquisition. A portion of the radiation 20 passes through or around the subject and impacts a detector array, represented generally at reference numeral 22. Detector elements of the array produce electrical signals that represent the intensity of the incident X-ray beam. These signals are acquired and processed to reconstruct an image of the features within the subject.

The distributed X-ray source 12 is controlled by a system controller 24, which furnishes both power, focal spot location, and control signals for CT examination sequences. Moreover, detector 22 is coupled to the system controller 24, which commands acquisition of the signals generated in the detector 22. The system controller 24 may also execute various signal processing and filtration functions, such as for initial adjustment of dynamic ranges, interleaving of digital image data, and so forth. In general, system controller 24 commands operation of the imaging system to execute examination protocols and to process acquired data. In the present context, system controller 24 also includes signal processing circuitry, typically based upon a general purpose or application-specific digital computer, associated memory circuitry for storing programs and routines executed by the computer, as well as configuration parameters and image data, interface circuits, and so forth.

In the embodiment illustrated in FIG. 1, system controller 24 is coupled to a linear positioning subsystem 26 and rotational subsystem 28. The rotational subsystem 28 enables the distributed X-ray source 12, collimator 14 and the detector 22 to be rotated one or multiple turns around the patient 18. It should be noted that the rotational subsystem 28 might include a gantry. Thus, the system controller 24 may be utilized to operate the gantry. The linear positioning subsystem 26 enables the patient 18, or more specifically a patient table, to be displaced linearly. Thus, the patient table may be linearly moved within the gantry to generate images of particular areas of the patient 18. Although the embodiment of the system described above is a modified third generation CT scanner, in which the distributed source 12 and the detector 22 both rotate, the methods to generate signals representative of cardiac motion described herein apply to all advanced generation CT systems.

As will be appreciated by those skilled in the art, the distributed source of radiation may be controlled by an X-ray controller 30 disposed within the system controller 24. Particularly, the X-ray controller 30 is configured to provide power, focal spot location, and timing signals to the distributed X-ray source 12. A motor controller 32 may be utilized to control the movement of the rotational subsystem 28 and the linear positioning subsystem 26.

Further, the system controller 24 is also illustrated comprising a data acquisition system 34. In this exemplary embodiment, the detector 22 is coupled to the system controller 24, and more particularly to the data acquisition system 34. The data acquisition system 34 receives data collected by readout electronics of the detector 22. The data acquisition system 34 typically receives sampled analog signals from the detector 22 and converts the data to digital signals for subsequent processing by a computer 36.

The computer 36 is typically coupled to the system controller 24. The data collected by the data acquisition system 34 may be transmitted to the computer 36 for subsequent processing and reconstruction. The computer 36 may comprise or communicate with a memory 38 that can store data processed by the computer 36 or data to be processed by the computer 36. It should be understood that any type of computer accessible memory device capable of storing the desired amount of data and/or code may be utilized by such an exemplary system 10. Moreover, the memory 38 may comprise one or more memory devices, such as magnetic or optical devices, of similar or different types, which may be local and/or remote to the system 10. The memory 38 may store data, processing parameters, and/or computer programs comprising one or more routines for performing the processes described herein.

The computer 36 may also be adapted to control features enabled by the system controller 24, i.e., scanning operations and data acquisition. Furthermore, the computer 36 may be configured to receive commands and scanning parameters from an operator via an operator workstation 40 typically equipped with a keyboard and other input devices (not shown). An operator may thereby control the system 10 via the input devices. Thus, the operator may observe the reconstructed image and other data relevant to the system from computer 36, initiate imaging, and so forth.

A display 42 coupled to the operator workstation 40 may be utilized to observe the reconstructed image. Additionally, the scanned image may also be printed by a printer 44 which may be coupled to the operator workstation 40. The display 42 and printer 44 may also be connected to the computer 36, either directly or via the operator workstation 40. Further, the operator workstation 40 may also be coupled to a picture archiving and communications system (PACS) 46. It should be noted that PACS 46 might be coupled to a remote system 48, radiology department information system (RIS), hospital information system (HIS) or to an internal or external network, so that others at different locations may gain access to the image data.

It should be further noted that the computer 36 and operator workstation 40 may be coupled to other output devices, which may include standard, or special purpose computer monitors and associated processing circuitry. One or more operator workstations 40 may be further linked in the system for outputting system parameters, requesting examinations, viewing images, and so forth. In general, displays, printers, workstations, and similar devices supplied within the system may be local to the data acquisition components, or may be remote from these components, such as elsewhere within an institution or hospital, or in an entirely different location, linked to the image acquisition system via one or more configurable networks, such as the Internet, virtual private networks, and so forth.

Figure 2:
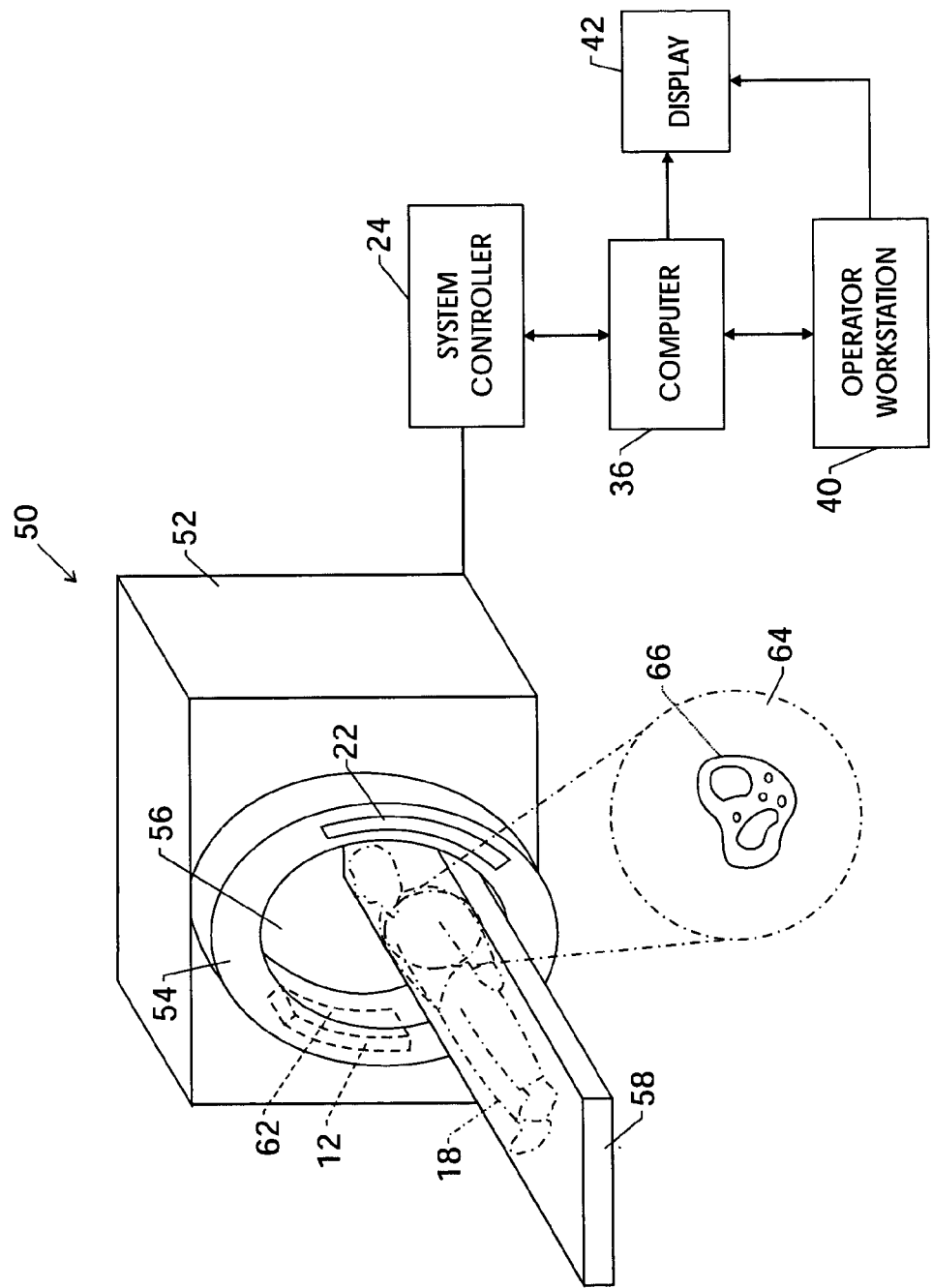
FIG. 2 is another diagrammatical view of a physical implementation of the CT system of FIG. 1, in accordance with one aspect of the present technique.

Referring generally to FIG. 2, an exemplary imaging system utilized in a present embodiment may be a CT scanning system 50. The CT scanning system 50 may be a volumetric CT (VCT) system utilizing a cone-beam geometry and an area detector to allow the imaging of a volume, such as an entire internal organ. Furthermore, as noted above, the CT scanning system 50 may be a modified third generation CT imaging system, as depicted, or may be a later generation CT imaging system.

The CT scanning system 50 is illustrated with a frame 52 and a gantry 54 that has an aperture 56 through which a patient 18 may be moved. A patient table 58 may be positioned in the aperture 56 of the frame 52 and the gantry 54 to facilitate movement of the patient 18, such as via linear displacement of the table 58 by the linear positioning subsystem 26 (see FIG. 1). The gantry 54 is illustrated with a distributed source of radiation 12, typically one or more X-ray sources that emit X-ray radiation from one or more focal points 62. The distributed X-ray source 12 may change the location of a focal point 62 instantaneously, either longitudinally or along the arc of the gantry 54. For cardiac imaging, the stream of radiation 16 is directed towards a cross section of the patient 18 including the heart.

In typical operation, distributed X-ray source 12 projects X-rays from the one or more focal points 62 and toward the detector array 22. The collimator 14 (see FIG. 1), such as lead or tungsten shutters, typically defines the size and shape of the projected X-rays that emerge from the distributed X-ray source 12. The detector 22, such as an area detector in the case of a VCT system, is generally formed by a plurality of detector elements, which detect the X-rays that pass through and around a subject of interest, such as the heart or chest. Each detector element produces an electrical signal that represents the intensity of the X-ray beam at the position of the element during the time the beam strikes the detector. The gantry 54 is rotated around the subject of interest so that a plurality of radiographic views may be collected by the computer 36.

Thus, as the distributed X-ray source 12 and the detector 22 rotate, the detector 22 collects data of the attenuated X-ray beams. Data collected from the detector 22 then undergoes pre-processing and calibration to condition the data to represent the line integrals of the attenuation coefficients of the scanned objects. The processed data, commonly called projections, may then be filtered and backprojected to formulate an image of the scanned area. A formulated image may incorporate, in certain modes, projection data acquired for an angular rotation of the gantry of less or more than 360 degrees.

Once reconstructed, the cardiac image produced by the system of FIGS. 1 and 2 reveals the heart of the patient 18. As illustrated generally in FIG. 2, the image 64 may be displayed to show patient features, such as indicated at reference numeral 66 in FIG. 2. In traditional approaches to diagnosis of medical conditions, such as disease states, and more generally of medical conditions or events, a radiologist or physician would consider the reconstructed image 64 to discern characteristic features of interest. Such features 66 include coronary arteries or stenotic lesions of interest, and other features, which would be discernable in the image, based upon the skill and knowledge of the individual practitioner. Other analyses may be based upon capabilities of various CAD algorithms.

As will be appreciated by those skilled in the art, reconstruction of an image 64 may be complicated by a variety of factors. For example, reconstructed images 64 of dynamic tissue may include motion-related image artifacts that are attributable to the movement of the tissue during imaging. To reduce motion-related artifacts, it is generally desirable to improve the temporal resolution of the CT reconstruction process.

Figure 3:
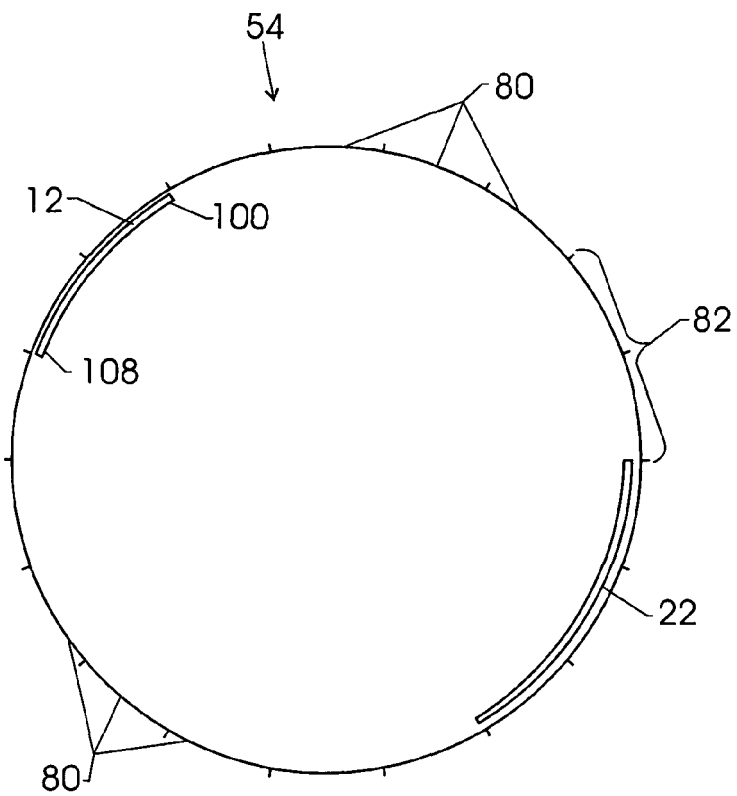
FIG. 3 is a diagrammatical view of an exemplary CT gantry, in accordance with one aspect of the present technique.

To address this problem, the present technique uses a projection data set, along with frequency content and phase information associated with the projection data set, to generate a set of temporally interpolated projections. The temporally interpolated projections may be reconstructed to form images with a high temporal resolution, typically less than 50 ms. One approach of the present technique utilizes a CT gantry 54 in which the scan path of the gantry 54 is divided into a discrete number, N, of uniformly sized arcs 80, as depicted in FIG. 3. For example, as depicted in FIG. 3, N equals 18. The distributed X-ray source 12 may be sized to cover two arc lengths 82. Alternatively, the distributed source 12 may cover less than or more than two arc lengths if alternative sampling schemes are employed during acquisition of the radiographs.

Figure 4:
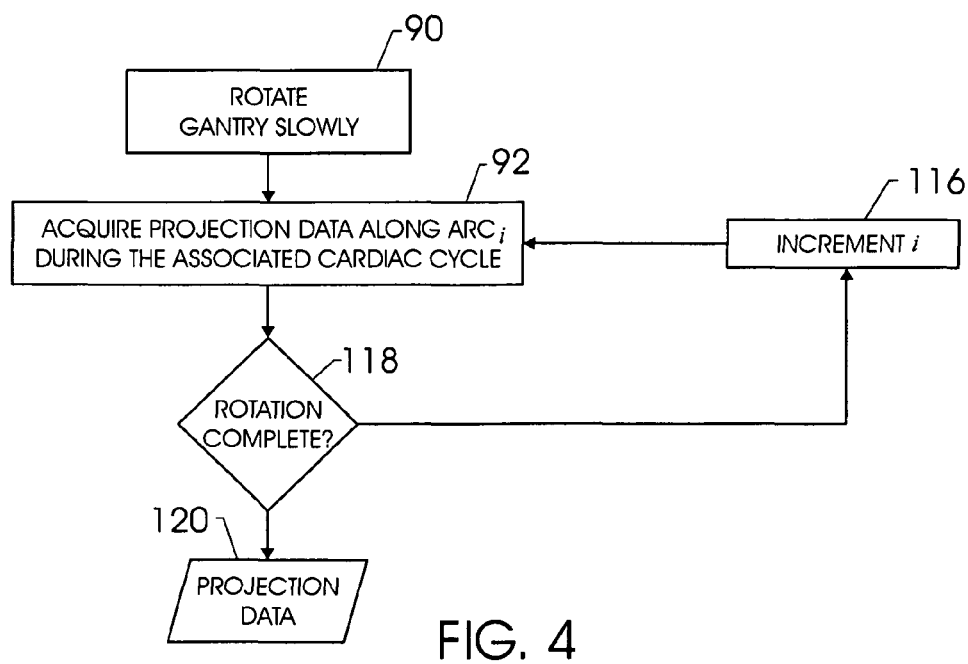
FIG. 4 is a flowchart depicting the acquisition of a projection data set, in accordance with one aspect of the present technique.

In the present technique, as depicted at step 90 of FIG. 4, the distributed X-ray source 12 is slowly rotated about a subject to generate radiographs, which may subsequently be processed into interpolated projection data. For example, the distributed X-ray source 12 may execute a single rotation about the subject, during which multiple cardiac cycles may occur. The rotation rate of the distributed source X-ray source 12, and the detector 22 in suitably modified third generation CT systems, may be greater than eight seconds, and may be between ten seconds and thirty seconds in one implementation. In particular, the rotation rate may equal the time required for one cardiac cycle of the subject multiplied by the number of arc lengths, N.

Projection data is repeatedly acquired as the distributed source 12 passes along each arc 80, as depicted at step 92. If the rotation rate of the distributed source 12 equals the time required for one cardiac cycle multiplied by N, the start of a new cardiac cycle should coincide with the start of projection acquisition along the next arc 80. The position of the focal point 62 on the distributed X-ray source 12 may be continually adjusted as the gantry 54 rotates so that each sampled view position relative to the object being scanned is identical.

Figure 5:
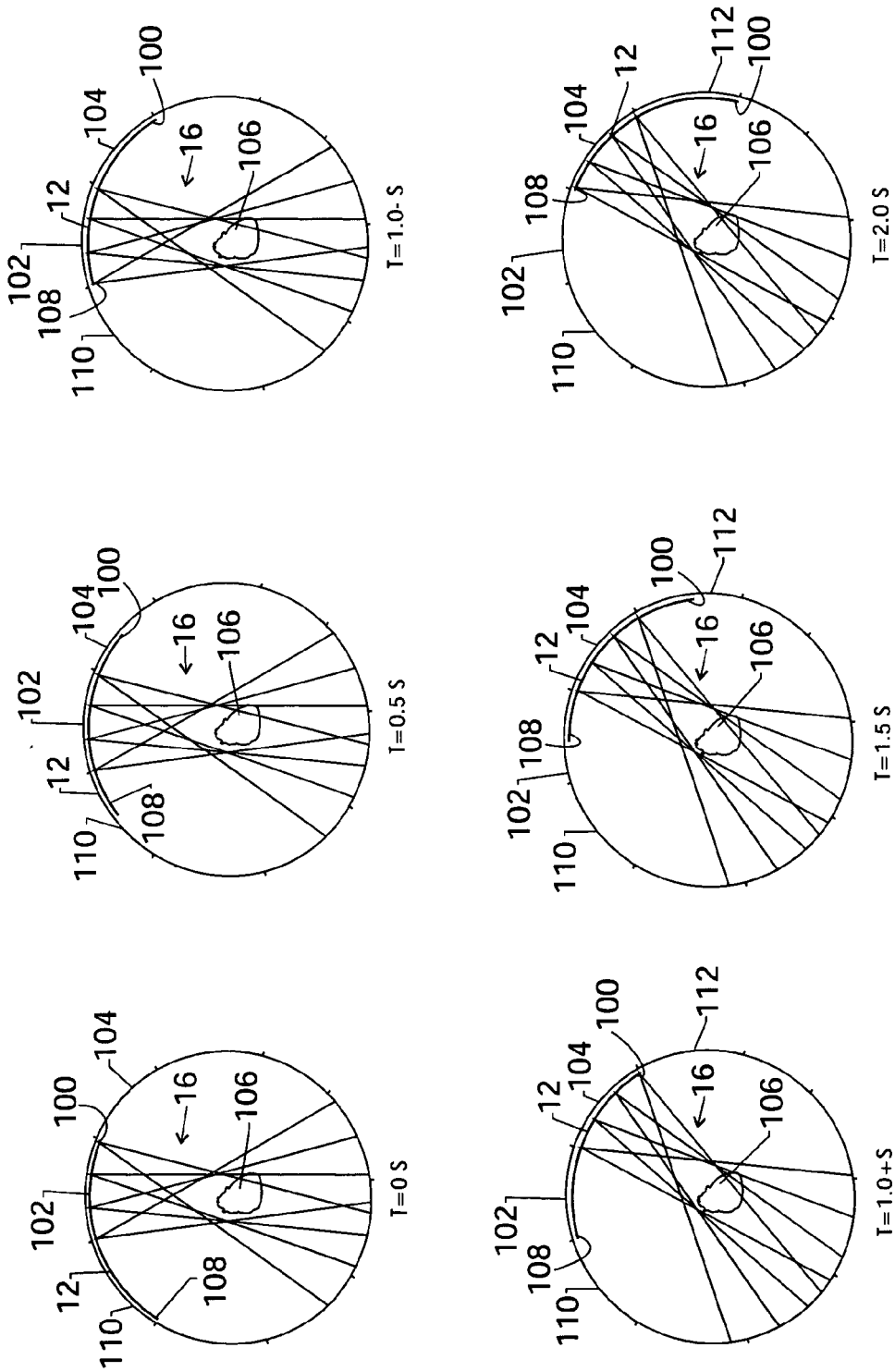
FIG. 5 is a sequence of views of the operation of a distributed X-ray source over the course of two cardiac cycles, in accordance with one aspect of the present technique.

For example, referring to FIG. 5, the rotation and acquisition process at two sequential arcs 80 is depicted. To simplify presentation, the cardiac cycle is presumed to be one second. At the outset, i.e., T=0 seconds, the leading edge 100 of the distributed X-ray source 12 coincides with the boundary between the first arc 102 and the second arc 104, such that the first arc 102 is covered by half of the distributed X-ray source 12. The portion of the distributed X-ray source 12 coinciding with the first arc 102 emits X-rays 16 through the volume of the thorax including the subject's heart 106 by triggering the focal spots along the arc in some predefined order. The portion of the distributed X-ray source 12 that has yet to enter the first arc 102 does not emit X-rays 16.

At T=0.5 seconds, the distributed X-ray source 12 has rotated halfway through the first arc 102 such that the middle portion of the distributed X-ray source 12 coincides with the first arc 102. The portion of the distributed X-ray source 12 coinciding with the first arc 102 continues to emit X-rays 16 through the volume of the thorax occupied by the subject's heart 106. That portion of the distributed X-ray source 12 which has not yet entered the first arc 102 or which has passed into the second arc 104 does not emit X-rays 16.

At T=1.0⁻ seconds, i.e., immediately before 1.0 seconds and the start of the next cardiac cycle, the trailing edge 108 of the distributed X-ray source 12 coincides with the boundary between the first arc 102 and the preceding arc 110. The portion of the distributed X-ray source 12 coinciding with the first arc 102 continues to emit X-rays 16 through the volume of the thorax occupied by the subject's heart 106. That portion of the distributed X-ray source 12 which has passed into the second arc 104 does not emit X-rays 16.

Because the X-ray source 12 is distributed, the switching of the arc positions at T=1.0 seconds occurs instantaneously. As a result, at T=1.0⁺ seconds, i.e., immediately after 1.0 seconds, the leading edge 100 of the distributed X-ray source 12 coincides with the boundary between the second arc 104 and the subsequent arc 112. The acquisition of projections along the second arc 104 thereafter precedes as described with regard to the first arc 102, as depicted at T=1.5 seconds and T=2.0⁻ seconds. In this manner, projection data is acquired along each arc 80 repeatedly during the respective cardiac cycle, as depicted at step 92 in FIG. 4. If the rotation or rotations are not complete, projection data may be acquired for the next arc 80 and cardiac cycle, as incremented at step 116, until the rotation or rotations are complete, as determined at decision block 118. The result is a projection data set 120 that comprises projections acquired at different instants in time with respect to the cardiac cycle at each view position.

Although the distributed X-ray source 12 is shown to cover two arc segments 80 in FIG. 3 and in FIG. 5, the distributed source 12 can be made slightly larger than this to account for variations in the cardiac cycle during the data acquisition process. Alternatively, the distributed X-ray source 12 may be sized to cover one arc segment 80, or slightly larger than one arc segment 80 to account for variations in the cardiac cycle during data acquisition, and used in conjunction with alternative sampling routines to achieve the same effective sampling data set.

Figure 6:
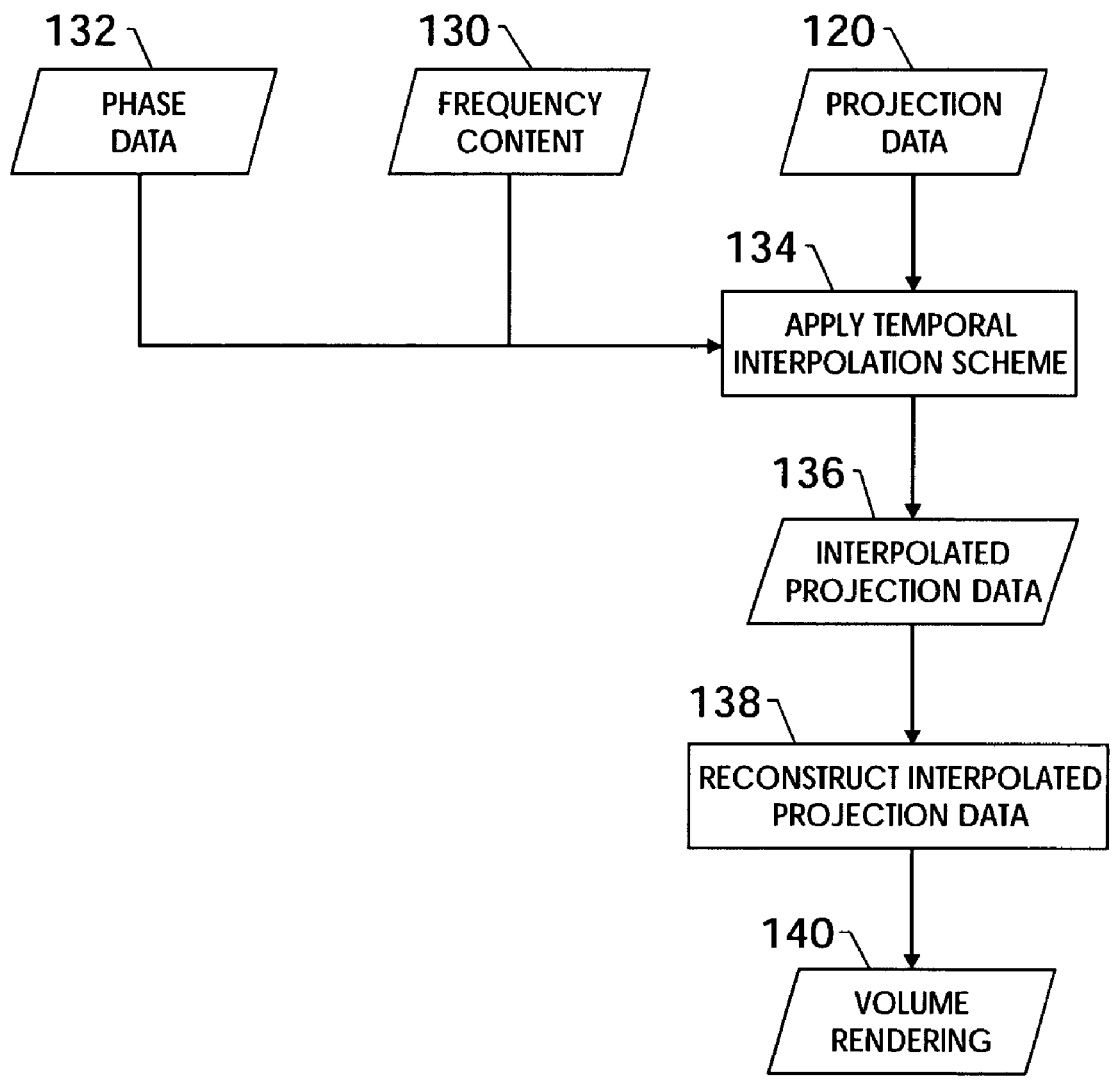
FIG. 6 is a flowchart depicting the generation and reconstruction of an interpolated projection data set.

The frequency content 130 of the projection data, i.e., a priori information about characteristics of motion in the heart as represented in the signals measured by elements of detector 22, and the cardiac phase data 132, i.e., the timing of the cardiac phases during the acquisition of the projection data 120, may be used to interpolate the projection data 120, as depicted in FIG. 6. The phase data 132 may comprise an ECG signal acquired concurrently with the radiographs. Alternatively, phase data 132 may be derived from the projection data 120, such as via techniques employing consistency conditions to analyze the projection data 120 and/or to compare the moments of the projection data 120.

Using the phase data 132 and information about the frequency content 130 in the projection data, the projections are correlated with the times that they correspond to in the cardiac cycle as well as with the angular positions of the gantry 54 to which they correspond. The projection data 120 may then be interpolated, as depicted at step 134, to generate interpolated projections 136. Because the two-dimensional projections appropriately capture the frequency content 130 in the signal acquired at each detector element, the interpolated projections 136 each correctly characterize the projection data at any instant in time with respect to the cardiac cycle at the respective view location. In this manner, projections acquired at discrete points in time may be converted into a continuous-time representation and, from the continuous time representation, the projections may be interpolated to a particular instant with respect to the cardiac cycle.

The conversion of discrete points into a continuous-time representation may be accomplished in a variety of ways known in the art. Likewise, the interpolation of values from a continuous-time representation using a suitable interpolation algorithm may be accomplished in various ways. For example, the Nyquist Theorem provides that, if a sufficiently high rate of discrete samples of a waveform are obtained, a continuous-time representation using the discrete-time samples may be generated. The Nyquist Theorem also provides that the value of any sample along the continuous-time representation can be interpolated at any point in time by selecting the sample value on the continuous-time representation that corresponds to the point in time. For example, a Fourier time series is a suitable continuous-time function for this purpose if the motion is periodic.

As noted above, the interpolated projections 136 each correspond to a particular instant of the cardiac cycle at a respective view angle. The interpolated projections 136 corresponding to a desired instant of the cardiac cycle may therefore be reconstructed, as depicted at step 138, to generate cardiac images at the desired instant of the cardiac cycle. The reconstructed images may, if desired be associated spatially and/or temporally to generate an image over time, a volume 140 at an instant in time, or a volume 140 over time. In addition, because the interpolated projections 136 are interpolated to the same instant in time, the reconstructed images and/or volumes have a high temporal resolution, typically less than 50 ms. Therefore the reconstructed images and/or volumes are substantially free of motion defects and artifacts, effectively "freezing" the cardiac motion at each point in time.

In addition, the interpolation process provides a mechanism to reduce quantum noise in the projection data. For example, a priori information about the frequency content of the projection data 120 may be used to bandlimit frequency components in the projection data 120. Bandlimiting the frequency components may help reduce noise in the reconstructed images and may allow patient dose to be reduced while still achieving suitable quality of reconstructed images.

While the present techniques have been presented in the context of cardiac imaging, the techniques may be applied to the imaging of other dynamic objects. Discussion of cardiac imaging is presented merely to facilitate explanation of the present techniques. Indeed, while the invention may be susceptible to various modifications and alternative forms, specific embodiments have been shown by way of example in the drawings and have been described in detail herein. However, it should be understood that the invention is not intended to be limited to the particular forms disclosed. Rather, the invention is to cover all modifications, equivalents, and alternatives falling within the spirit and scope of the invention as defined by the following appended claims.

What is claimed is:

1. A method for acquiring a projection data set, comprising:
    rotating a distributed X-ray source and a detector array about a volume containing a heart having a cardiac cycle, wherein a rotational period of the distributed X-ray source comprises a length of time required for image reconstruction and is approximately a multiple of the cardiac cycle, wherein the distributed X-ray source comprises a plurality of addressable X-ray focal spots;
    emitting X-rays from the distributed X-ray source;
    acquiring a projection data set comprising a plurality of projections generated from the emitted X-rays at each view location of a gantry;
    generating a set of interpolated projections by interpolating the projection data set using phase information from the projection data set or from a set of concurrently acquired phase data and apriori frequency content of the projection data set, wherein each interpolated projection characterizes the projection data at a particular view location of the gantry and at a particular time; and
    reconstructing the set of interpolated projections to generate one or more images.

2. The method as recited in claim 1, further comprising:
    associating two or more images to generate a volume rendering.

3. The method as recited in claim 1, wherein interpolating the projection data set comprises reducing statistical noise in the projection data set.

4. The method as recited in claim 3 further comprising reducing an X-ray dose applied to the volume of interest in response to the reduction in statistical noise.

5. The method according to claim 1, wherein a scan path of the distributed X-ray source and the detector array is subdivided into a number of arcs, and wherein the rotational period is approximately equal to a time required for one cardiac cycle multiplied by the numbers of arcs.

6. The method according to claim 1, further comprising adjusting the addressable X-ray focal spots of the distributed X-ray source so that a particular view location of one or more view locations provided by the gantry relative to the heart is substantially identical.

7. The method according to claim 1, wherein the projections are acquired at discrete points in time, converted into a continuous-time representation, and interpolated to said particular time with respect to the cardiac cycle.

8. A computer program, provided on one or more non-transitory computer readable media, for acquiring a projection data set, comprising:
    a routine for rotating a distributed X-ray source and a detector array about a volume containing a heart having a cardiac cycle, wherein a rotational period of the distributed X-ray source comprises a length of time required for image reconstruction and is approximately a multiple of the cardiac cycle, wherein the distributed X-ray source comprises a plurality of addressable X-ray focal spots;
    a routine for emitting X-rays from the distributed X-ray source, wherein said addressable X-ray focal spots of the distributed X-ray source are activated so that one or more view locations relative to the heart is substantially identical;
    a routine for acquiring a projection data set comprising a plurality of projections generated from the emitted X-rays at each view location of a gantry;
    a routine for generating a set of interpolated projections by interpolating the projection data set using phase information from the projection data set or from a set of concurrently acquired phase data and apriori knowledge of frequency content of the projection data set, wherein each interpolated projection characterizes the projection data at a particular view location of the gantry and at a particular time; and
    a routine for reconstructing the set of interpolated projections to generate one or more images.

9. The computer program as recited in claim 8, a further comprising:
    a routine for associating two or more images to generate a volume rendering.

10. The computer program as recited in claim 8, wherein the routine for generating a set of interpolated projections reduces statistical noise in the projection data set.

11. The computer program as recited in claim 10, further comprising a routine for reducing an X-ray dose applied to the volume of interest in response to the reduction in statistical noise.

12. A CT image analysis system of volume containing a heart, comprising:
    a distributed X-ray source, disposed on a gantry and providing multiple projection data sets scanned over an angular coverage of the gantry less than about 360 degrees, wherein a rotational period of the distributed X-ray source about a volume containing the heart comprises a length of time required for image reconstruction, wherein the distributed X-ray source comprises a plurality of addressable X-ray focal spots;
    a detector configured to detect the radiation emitted by distributed X-ray source and to generate one or more signals responsive to the radiation, wherein the detector comprises a plurality of detector elements;
    a system controller configured to control the X-ray source and detector and to acquire a set of projection data during rotation of the X-ray source and detector about a volume containing the heart comprising a length of time required for image reconstruction from one or more of the detector elements via a data acquisition system; and
    a computer system configured to receive the set of projection data; wherein the computer system is further configured to generate a set of interpolated projections by interpolating the set of projection data using phase information from the projection data set or from a set of concurrently acquired phase data and apriori knowledge of a frequency content of the set of projection data, wherein each interpolated projection characterizes the projection data at a particular view location of the gantry and at a particular time and to reconstruct the set of interpolated projections to generate one or more images.

13. The CT image analysis system as recited in claim 12, wherein the computer system is further configured to associate two or more images to generate a volume rendering.

14. The CT image analysis system as recited in claim 12, wherein generating a set of interpolated projections reduces statistical noise in the set of projection data.

15. The CT image analysis system as recited in claim 14, wherein the computer is further configured to reduce an X-ray dose applied to the volume of interest in response to the reduction in statistical noise.

16. A CT image analysis system, comprising:
    means for rotating a distributed X-ray source and detector about a volume containing a heart having a cardiac cycle, wherein the rotational period of the distributed X-ray source comprises a length of time required for image reconstruction, wherein the distributed X-ray source comprises a plurality of addressable X-ray focal spots;

means for emitting X-rays from the distributed X-ray source;

means for acquiring a projection data set comprising a plurality of projections generated from the emitted X-rays;

means for activating the addressable X-ray focal spots to acquire a collection of projection data at each view location of a gantry;

means for generating a set of interpolated projections using phase information from the projection data set or from a set of concurrently acquired phase data and apriori knowledge of a frequency content of the projection data set;

means for reconstructing the set of interpolated projections to generate one or more images.

* * * * *

UNITED STATES PATENT AND TRADEMARK OFFICE
CERTIFICATE OF CORRECTION

PATENT NO. : 7,813,473 B2
APPLICATION NO. : 10/625321
DATED : October 12, 2010
INVENTOR(S) : Edic et al.

It is certified that error appears in the above-identified patent and that said Letters Patent is hereby corrected as shown below:

In Column 9, Line 30, in Claim 4, delete "claim 3" and insert -- claim 3, --, therefore.

In Column 10, Line 9, in Claim 9, delete "a further" and insert -- further --, therefor.

In Column 10, Line 31, in Claim 12, delete "the radiation" and insert -- radiation --, therefor.

Signed and Sealed this

Seventh Day of December, 2010

David J. Kappos
*Director of the United States Patent and Trademark Office*